(12) United States Patent
Donahue

(10) Patent No.: US 9,814,506 B2
(45) Date of Patent: *Nov. 14, 2017

(54) BONE IMPLANTS

(71) Applicant: DePuy Synthes Products, Inc., Raynham, MA (US)

(72) Inventor: James R. Donahue, East Falmouth, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 64 days.

This patent is subject to a terminal disclaimer.

(21) Appl. No.: 14/716,188

(22) Filed: May 19, 2015

(65) Prior Publication Data

US 2015/0245860 A1 Sep. 3, 2015

Related U.S. Application Data

(63) Continuation of application No. 13/223,831, filed on Sep. 1, 2011, now Pat. No. 9,060,818.

(51) Int. Cl.
| | |
|---|---|
| *A61B 17/84* | (2006.01) |
| *A61B 17/86* | (2006.01) |
| *A61B 17/04* | (2006.01) |
| *A61F 2/08* | (2006.01) |
| *A61B 17/70* | (2006.01) |

(52) U.S. Cl.
CPC ...... *A61B 17/8605* (2013.01); *A61B 17/7032* (2013.01); *A61B 17/7086* (2013.01); *A61B 17/7037* (2013.01)

(58) Field of Classification Search
CPC .. A61B 17/70–17/7046; A61B 17/84–17/8695
USPC .................................. 606/246–278, 300–321
See application file for complete search history.

(56) References Cited

U.S. PATENT DOCUMENTS

| | | |
|---|---|---|
| 5,176,679 A | 1/1993 | Lin |
| 5,261,913 A | 11/1993 | Marnay |
| 5,360,431 A | 11/1994 | Puno et al. |
| 5,397,363 A | 3/1995 | Gelbard |

(Continued)

FOREIGN PATENT DOCUMENTS

| | | |
|---|---|---|
| WO | 96/02198 A1 | 2/1996 |
| WO | 97/37604 A1 | 10/1997 |

(Continued)

OTHER PUBLICATIONS

International Search Report and Written Opinion for Application No. PCT/US2012/52448, mailed Nov. 6, 2012 (19 pages).

*Primary Examiner* — Eduardo C Robert
*Assistant Examiner* — Michelle C Eckman
(74) *Attorney, Agent, or Firm* — Nutter McClennen & Fish LLP

(57) ABSTRACT

Various bone fixation devices and methods of using the same are provided. In one embodiment, a spinal implant assembly is provided having a generally U-shaped rod-receiving head or receiver member, and a bone-engaging member extending distally from the receiver member. The receiver member can have two side arms extending proximally from a distal end, and the arms can define a U-shaped channel therebetween for receiving a spinal fixation element. The side arms of the receiver can have various configurations and can include a number of features to facilitate mating with a spinal tool.

19 Claims, 10 Drawing Sheets

(56) References Cited

U.S. PATENT DOCUMENTS

| | | | |
|---|---|---|---|
| 5,466,237 A | 11/1995 | Byrd, III et al. |
| 5,474,555 A | 12/1995 | Puno et al. |
| 5,545,165 A | 8/1996 | Biedermann et al. |
| 5,554,157 A | 9/1996 | Errico et al. |
| 5,586,984 A | 12/1996 | Errico et al. |
| 5,643,260 A | 7/1997 | Doherty |
| 5,643,264 A | 7/1997 | Sherman et al. |
| 5,647,873 A | 7/1997 | Errico et al. |
| 5,669,911 A | 9/1997 | Errico et al. |
| 5,672,176 A | 9/1997 | Biedermann et al. |
| 5,676,703 A | 10/1997 | Gelbard |
| 5,690,630 A | 11/1997 | Errico et al. |
| 5,716,356 A | 2/1998 | Biedermann et al. |
| 5,725,527 A | 3/1998 | Biedermann et al. |
| 5,728,098 A | 3/1998 | Sherman et al. |
| 5,738,685 A | 4/1998 | Halm et al. |
| 5,797,911 A | 8/1998 | Sherman et al. |
| 5,817,094 A | 10/1998 | Errico et al. |
| 5,863,293 A | 1/1999 | Richelsoph |
| 5,879,350 A | 3/1999 | Sherman et al. |
| 5,885,286 A | 3/1999 | Sherman et al. |
| 5,899,904 A | 5/1999 | Errico et al. |
| 5,899,905 A | 5/1999 | Errico et al. |
| 5,925,047 A | 7/1999 | Errico et al. |
| 6,019,762 A | 2/2000 | Cole |
| 6,053,917 A | 4/2000 | Sherman et al. |
| 6,302,888 B1 | 10/2001 | Mellinger et al. |
| 6,443,953 B1 | 9/2002 | Perra et al. |
| 6,478,797 B1 | 11/2002 | Paul |
| 6,485,491 B1 * | 11/2002 | Farris | A61B 17/7002 606/250 |
| 6,520,963 B1 | 2/2003 | McKinley |
| 6,540,749 B2 | 4/2003 | Schafer et al. |
| 6,554,834 B1 | 4/2003 | Crozet et al. |
| 6,660,004 B2 | 12/2003 | Barker et al. |
| 6,695,843 B2 | 2/2004 | Biedermann et al. |
| 6,786,903 B2 | 9/2004 | Lin |
| 6,843,791 B2 | 1/2005 | Serhan |
| 6,918,911 B2 | 7/2005 | Biedermann et al. |
| 6,974,460 B2 | 12/2005 | Carbone et al. |
| 6,997,927 B2 | 2/2006 | Jackson |
| 7,204,838 B2 | 4/2007 | Jackson |
| 7,291,151 B2 | 11/2007 | Alvarez |
| 7,476,239 B2 | 1/2009 | Jackson |
| 7,479,156 B2 | 1/2009 | Lourdel et al. |
| 7,513,905 B2 | 4/2009 | Jackson |
| 7,572,279 B2 | 8/2009 | Jackson |
| 7,588,575 B2 | 9/2009 | Colleran et al. |
| 7,618,442 B2 | 11/2009 | Spitler et al. |
| 7,625,394 B2 | 12/2009 | Molz, IV et al. |
| 9,060,818 B2 | 6/2015 | Donahue |
| 2002/0026193 A1 | 2/2002 | Barker et al. |
| 2002/0116001 A1 | 8/2002 | Schafer et al. |
| 2004/0167525 A1 | 8/2004 | Jackson |
| 2004/0249378 A1 | 12/2004 | Saint Martin et al. |
| 2005/0049588 A1 | 3/2005 | Jackson |
| 2005/0131410 A1 | 6/2005 | Lin |
| 2005/0177154 A1 | 8/2005 | Moumene et al. |
| 2005/0277927 A1 | 12/2005 | Guenther et al. |
| 2006/0036242 A1 | 2/2006 | Nilsson et al. |
| 2006/0064089 A1 | 3/2006 | Jackson |
| 2006/0100622 A1 | 5/2006 | Jackson |
| 2006/0111715 A1 | 5/2006 | Jackson |
| 2006/0129149 A1 * | 6/2006 | Iott | A61B 17/7032 606/278 |
| 2006/0200133 A1 | 9/2006 | Jackson |
| 2006/0241603 A1 | 10/2006 | Jackson |
| 2006/0276789 A1 | 12/2006 | Jackson |
| 2006/0293659 A1 | 12/2006 | Alvarez |
| 2006/0293666 A1 | 12/2006 | Matthis et al. |
| 2007/0088357 A1 | 4/2007 | Johnson et al. |
| 2008/0147129 A1 | 6/2008 | Biedermann et al. |
| 2009/0143827 A1 * | 6/2009 | Levy | A61B 17/7037 606/308 |
| 2009/0198280 A1 | 8/2009 | Spratt et al. |
| 2009/0228051 A1 | 9/2009 | Kolb et al. |
| 2009/0299415 A1 | 12/2009 | Pimenta |
| 2010/0004692 A1 | 1/2010 | Biedermann et al. |
| 2010/0160980 A1 | 6/2010 | Walsh et al. |
| 2010/0179602 A1 | 7/2010 | Dauster et al. |
| 2010/0292740 A1 | 11/2010 | Garamszegi et al. |
| 2010/0312287 A1 | 12/2010 | Jackson |
| 2010/0318136 A1 | 12/2010 | Jackson et al. |
| 2011/0040328 A1 | 2/2011 | Miller et al. |
| 2011/0172718 A1 | 7/2011 | Felix et al. |
| 2011/0196430 A1 | 8/2011 | Walsh et al. |
| 2011/0196431 A1 | 8/2011 | Chao et al. |
| 2011/0208248 A1 * | 8/2011 | Barrus | A61B 17/7032 606/305 |
| 2011/0257690 A1 | 10/2011 | Rezach |
| 2012/0046699 A1 | 2/2012 | Jones et al. |
| 2012/0116462 A1 | 5/2012 | Arambula |
| 2012/0143264 A1 | 6/2012 | Matthis et al. |
| 2012/0197313 A1 * | 8/2012 | Cowan | A61B 17/7037 606/305 |
| 2012/0215263 A1 | 8/2012 | Lee |
| 2012/0245640 A1 | 9/2012 | Auerbach et al. |
| 2013/0060294 A1 | 3/2013 | Donahue |

FOREIGN PATENT DOCUMENTS

| | | |
|---|---|---|
| WO | 01/06940 A1 | 2/2001 |
| WO | 02/054966 A2 | 7/2002 |
| WO | 03/028566 A1 | 4/2003 |
| WO | 2005/074823 A1 | 8/2005 |
| WO | 2007/025132 A2 | 3/2007 |
| WO | 2007/047711 A2 | 4/2007 |
| WO | 2007/116437 A1 | 10/2007 |
| WO | 2007/118045 A1 | 10/2007 |

* cited by examiner

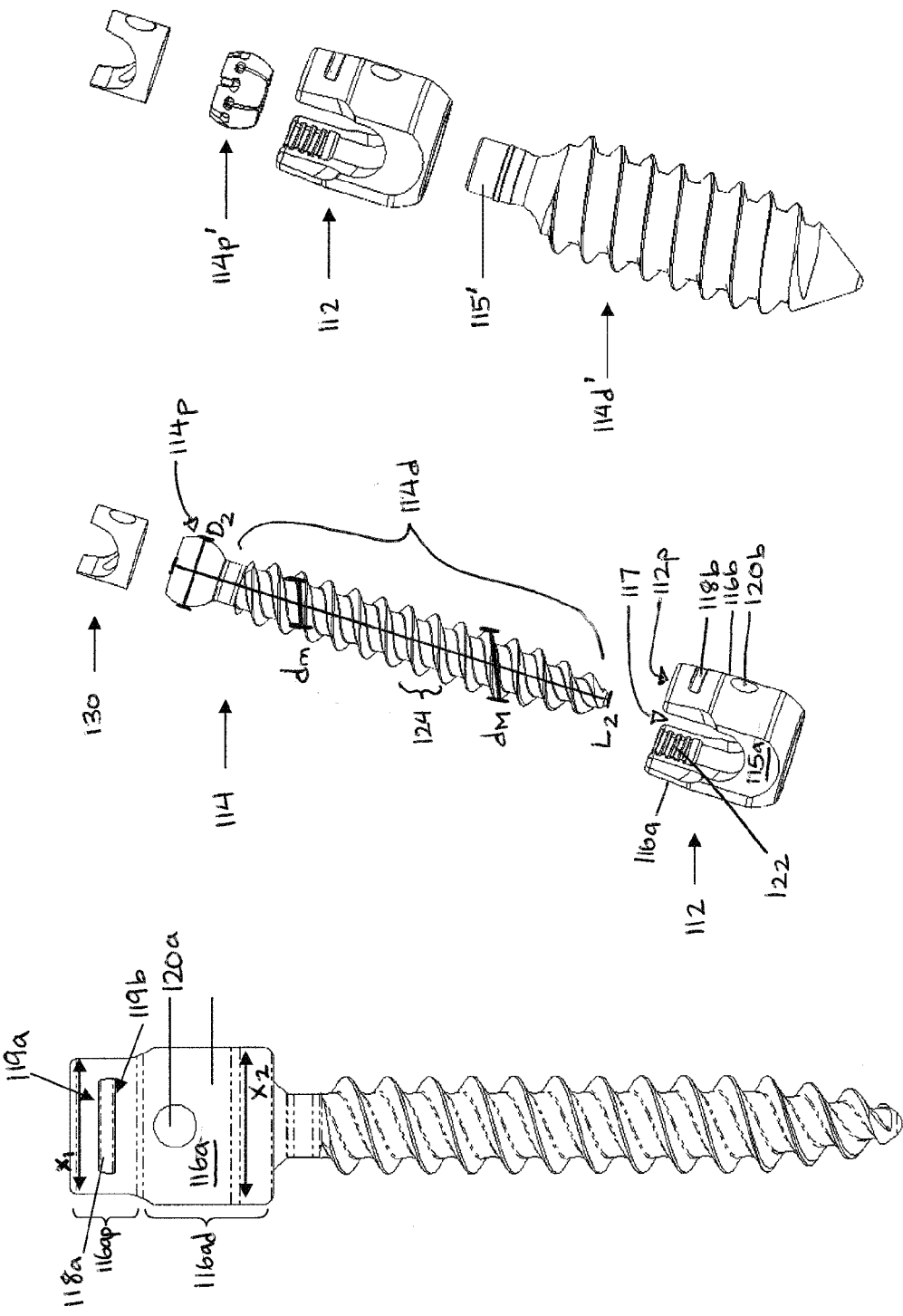

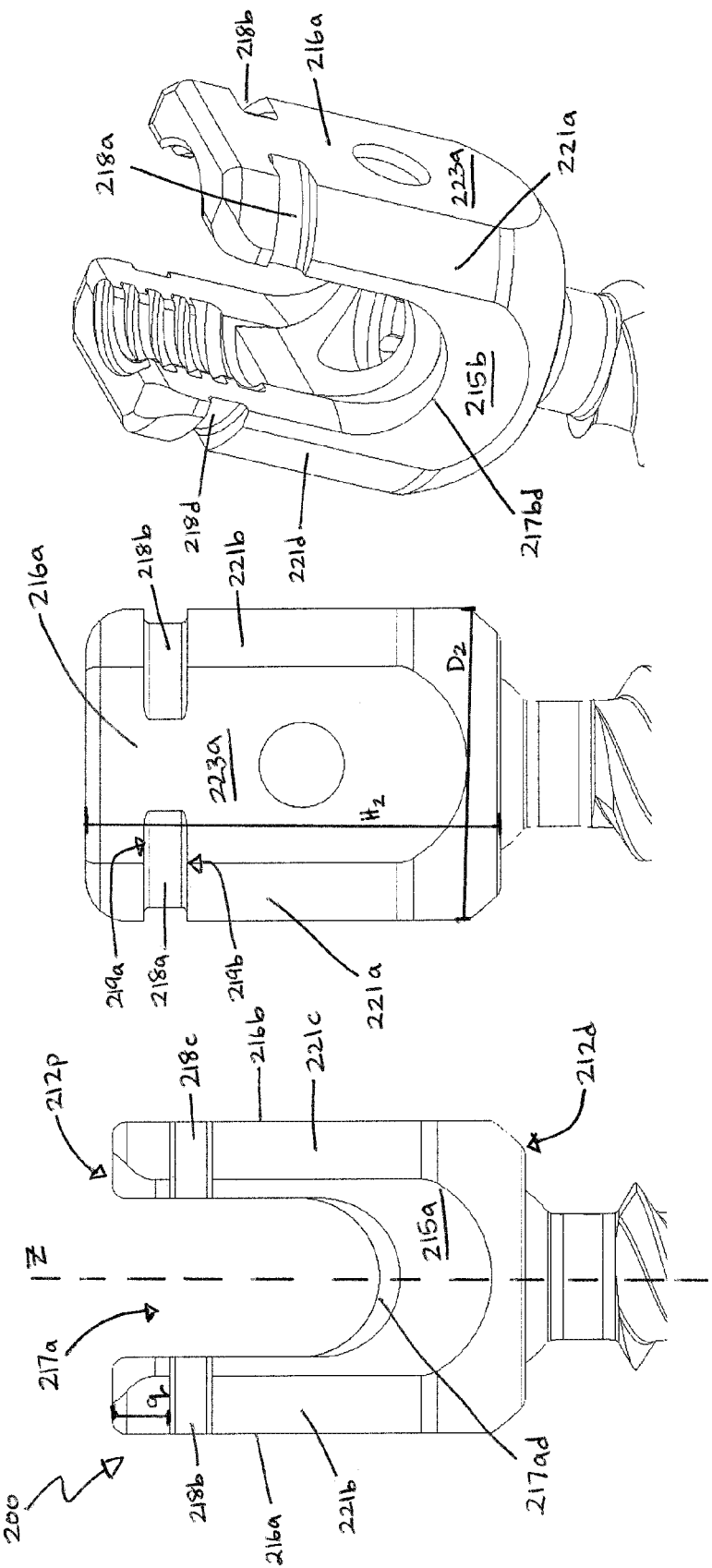

BONE IMPLANTS

CROSS-REFERENCE TO RELATED APPLICATIONS

This application is a continuation of U.S. application Ser. No. 13/223,831 filed on Sep. 1, 2011 and entitled "BONE IMPLANTS," which is hereby incorporated herein by reference in its entirety.

FIELD

The present invention relates to bone fixation devices and methods of using the same.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a bone screw with a threaded shank that is adapted to be threaded into a vertebra, and a rod-receiving element, usually in the form of a head having opposed U-shaped slots formed therein. The shank and rod-receiving assembly can be provided as a monoaxial assembly, whereby the rod-receiving element is fixed with respect to the shank, a unidirectional assembly, wherein the shank is limited to movement in a particular direction, e.g., within a single plane, or a polyaxial assembly, whereby the rod-receiving element has free angular movement with respect to the shank. In use, the shank portion of each screw is threaded into a vertebra, and once properly positioned, a fixation rod is seated into the rod-receiving element of each screw. The rod is then locked in place by tightening a set-screw, plug, or similar type of fastening mechanism onto the rod-receiving element.

During open and percutaneous pedicle screw procedures, it is standard practice to attach instruments to the implant head for rod approximation, head manipulation, or to locate a pathway to the head through the skin. This attachment needs to be robust enough to attach multiple types of instruments and withstand loading axially as well as side loading during compression/distraction maneuvers and derotation.

Accordingly, there remains a need for a pedicle fixation device having various robust attachment options for multiple instruments to be easily attached.

SUMMARY

The present invention provides various embodiments of spinal anchors and methods for implanting spinal anchors.

In one embodiment, a spinal implant is provided having a receiver member and a bone-engaging member extending distally from the receiver member and effective to engage a bone. The receiver member can have a base portion with first and second opposed side arms extending there from. The first and second opposed side arms can define opposed U-shaped rod-receiving recesses therebetween. The receiver member can also include one or more slots formed in a proximal portion of the outer surface of the first and second opposed side arms. The slot(s) can be configured to facilitate engagement of the receiver member by a tool, such as a rod-reduction device or various other tools used to implant or otherwise manipulate the spinal implant. The receiver member can also include various other features, such as a compression cap disposed within the receiver member and first and second bore holes formed in the outer surface of the first and second side arms. The bores holes can be configured to swage inward to lock the compression cap into the receiver member.

While the receiver member can have a variety of configurations, in one embodiment the receiver member has opposed planar outer surfaces surrounding the U-shaped rod receiving recesses, and an outer surface of each of the first and second opposed side arms is semi-cylindrical. At least a proximal portion of an outer surface of the first and second side arms can taper inward in a proximal direction such that a width of the proximal portion of the outer surface of each of the first and second side arms is less than a width of the distal portion of the outer surface of each of the first and second side arms. In an exemplary embodiment, the first and second side arms taper inward at a location proximal to a distal-most end of the U-shaped rod-receiving recesses and distal to the first and second slots. For example, the proximal portion of the outer surface of each of the first and second side arms can taper inward at an angle. While the angle can vary, in an exemplary embodiment the angle can be in a range of about 0 to 80 degrees, and more preferably about 0 to 45 degrees, and even more preferably about 0 to 10 degrees. In an exemplary embodiment, the outer surface of each of the first and second side arms tapers inward at an angle of about 4 degrees.

The slots can also have a variety of configurations. In one embodiment, the first slot has a planar inner surface that is parallel to a planar inner surface of the second slot. Each of the first and second slots can have opposed superior and inferior surfaces, and the superior and inferior surfaces can be parallel to one another along an entire length thereof, or the superior and inferior surfaces can diverge away from one another, e.g., at opposed ends thereof. In other aspects, the superior and inferior surfaces can extend at an angle with respect to one another. While the angle can vary, in an exemplary embodiment, the angle is in the range of about 0 to 120 degrees, and more preferably about 0 to 50 degrees, and most preferably about 20 degrees.

In another embodiment, the spinal implant can have a U-shaped receiver member having an open proximal end and a substantially closed distal end, with a longitudinal axis extending there between. A bone-engaging member can extend from the substantially closed distal end of the receiver member, and it can be effective to engage bone. The U-shaped receiver member can have opposed U-shaped cut-outs formed therein and configured to seat a spinal fixation rod. The U-shaped receiver member can also have first, second, third, and fourth distinct slots formed therein at a location proximal to a distal end of the U-shaped cut-outs. In one aspect, the U-shaped receiver member includes first and second side arms defining the U-shaped cut-outs, and the first side arm has the first and second slots formed therein, and the second side arm has the third and fourth slots formed therein. Each of the first and second side arms can have a planar outer surface extending between opposed substantially semi-cylindrical lateral outer surfaces. Each slot can be disposed across both a portion of the planar outer surface of one of the side arms and a portion of one of the opposed semi-cylindrical lateral outer surfaces of one of the first and second side arms. The first, second, third, and fourth slots can all extend in the same plane and can be spaced radially around the receiver member.

In another embodiment, a spinal implant is provided having a receiver member with first and second opposed side arms extending between an open proximal end and a distal end, and opposed U-shaped rod-receiving recesses formed between the first and second opposed side arms. The U-shaped rod-receiving recesses can extend from the open proximal end and terminating proximal to the distal end. In one aspect, each of the first and second opposed side arms has a distal planar outer surface and a tapering outer surface that extends proximally from the distal planar outer surface and that tapers inward in a proximal direction. Each side arm can also include a proximal lip formed on a proximal end thereof and extending laterally between opposed lateral edges of the side arm, and the proximal lip having an inferior surface that abuts the tapering outer surface. The implant can further include a bone-engaging member extending from the distal end of the receiver member and effective to engage bone In one embodiment, the inferior surface can extend at an angle relative to a superior surface of the proximal lip. While the angle can vary, in one embodiment the angle can be in the range of about 0 to 89 degrees, and more preferably about 0 to 30 degrees, and most preferably the angle is about 10 degrees. The distal planar surfaces of the first and second opposed side arms can be perpendicular to the inferior surface of the proximal lip on each of the first and second opposed side arms. Each of the first and second opposed side arms can also include a bore formed in the distal planar outer surface.

BRIEF DESCRIPTION OF THE DRAWINGS

The invention will be more fully understood from the following detailed description taken in conjunction with the accompanying drawings, in which:

FIG. 1C is a side view of the bone screw assembly of FIG. 1A, rotated 90 degrees;

FIG. 1D is an exploded perspective view of the bone screw assembly of FIG. 1A, shown in a top loading configuration;

FIG. 1E is an exploded perspective view of an alternate embodiment of a bone screw assembly similar to FIG. 1A, but shown in a bottom loading configuration;

FIG. 2A is a side view of another embodiment of a bone screw assembly having four distinct slots;

FIG. 2B is a side view of the bone screw assembly of FIG. 2A, rotated 90 degrees;

FIG. 2C is an isometric view of the bone screw assembly of FIG. 2A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary spinal implant devices and methods are provided. In general, the devices and methods provide various robust attachment options for multiple instruments to be easily attached. In general, spinal implants are provided that allow for attachment to various instruments for various reasons, such as for rod approximation, head manipulation, or to locate a pathway to the receiver head through the skin. The implants can allow for these attachments, while being robust enough to withstand axial loading as well as side loading during various surgical maneuvers and manipulations, such as compression/distraction and derotation.

The spinal implants disclosed herein include a generally U-shaped rod-receiving head or receiver member having an open proximal end and a distal end coupled to a bone-engaging member, such as a bone screw, bone hook, etc. The receiver member can have two side arms extending proximally from the distal end to the open proximal end, and defining a U-shaped channel therebetween to receive a spinal fixation element, such as a spinal rod. The side arms of the receiver can have various configurations and can include engagement features, such as slots or grooves, by which various tools can grasp the receiver member to manipulate the implant in various ways. Various configurations of the side arms can provide additional benefits, such as robustness or elimination of directionality when mating to various instruments.

Figure 1B:
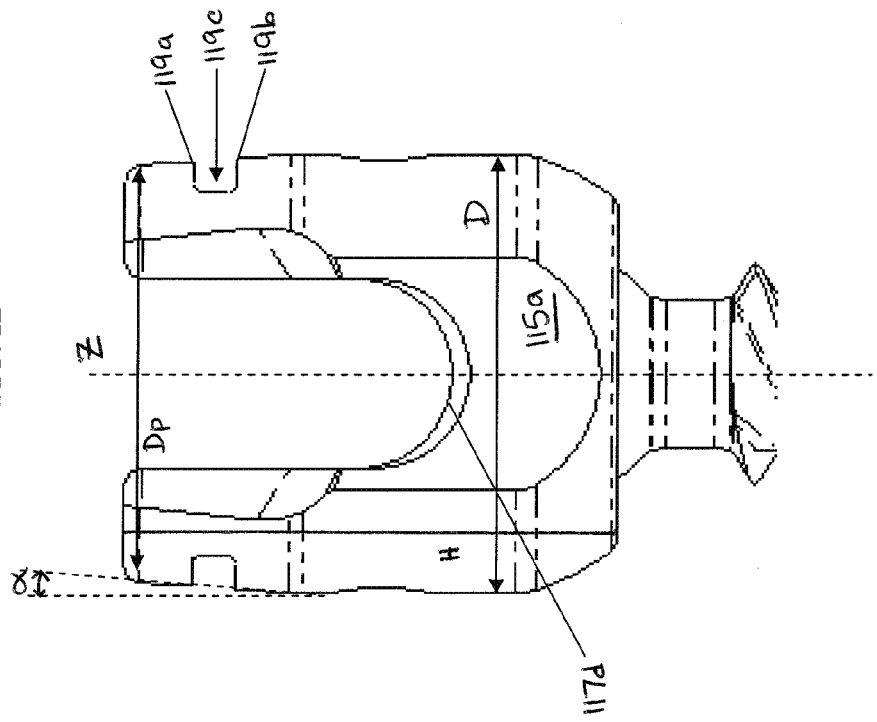
FIG. 1B is an enlarged view of the receiver member of FIG. 1A.
Figure 1A:
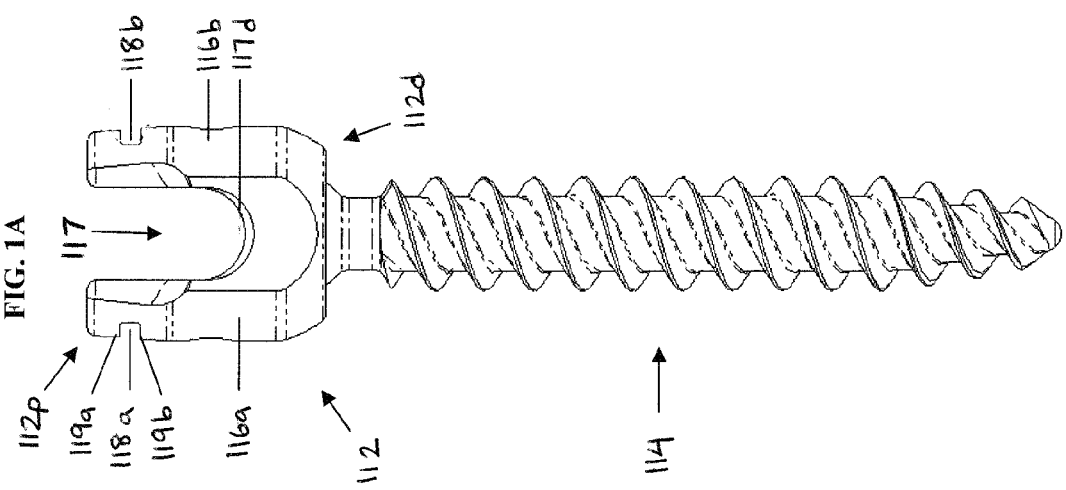
FIG. 1A is a side view of one embodiment of a bone screw assembly with a tapered receiver member.

FIGS. 1A-1D illustrate one embodiment of a bone screw assembly 100. As shown in FIG. 1A, the bone screw assembly 100 generally includes a receiver member 112 for receiving a spinal fixation element, such as a spinal rod, and a bone-engaging member 114 for engaging bone. The receiver member 112 and the bone-engaging member 114 can be joined in a variety of ways. For example, the bone-engaging member 114 can be fixedly mated to or integrally formed with the receiver member 112 to form a monoaxial assembly. Alternatively, it can be unidirectional, such that movement of the bone-engaging member is limited to a single direction, e.g., along a single plane, or it can be polyaxially coupled to the receiver member 112 to allow angular movement of the receiver member 112 relative to the bone-engaging member 114.

The receiver member 112 can have a variety of configurations. In the embodiment of FIGS. 1A-1D, the receiver member 112 is in the form of a substantially U-shaped head with opposed first and second side arms 116a, 116b that extend proximally from a substantially closed distal base portion or distal end 112d to an open proximal end 112p. The side arms 116a, 116b are separated by opposed U-shaped slots that define a U-shaped channel 117 extending through the receiver head 112 for seating a spinal fixation element, such as a rod. The slots that define the channel 117 can extend distally from the open proximal end 112p and they can terminate at a location proximal to the closed distal end 112d such that a spinal fixation element extending through the channel 117 is positioned a distance above the distal end 112d of the receiver 112. One skilled in the art will appreciate that the receiver member 112 can be configured to receive a variety of fixation elements. Suitable spinal fixation elements for use with the present invention include, by way of non-limiting examples, rods, tethers, cables, plates, etc. The spinal fixation elements can have a variety of configurations, and, by way of non-limiting example, can be rigid, semi-rigid, bendable, flexible, etc.

The substantially closed distal base portion 112d can have a variety of configurations, but in general the base portion 112d can have a substantially cylindrical shape. However, a distal portion of the outer surface of the base portion 112d can taper inward to have a truncated conical shape. The base portion can also include opposed planar sidewalls 115a, 115b (shown in FIGS. 1A and 1F) formed thereon. The planar sidewalls 115a, 115b can be positioned distal of the U-shaped slots that define channel 117, and the can extend partially around each slot. The planar sidewalls 115a, 115b can also be positioned to extend between opposed lateral edges of the side arms 116a, 116b. While not shown, the base portion 112d can have a concave cavity formed therein that seats a portion of the bone-engaging member 114, and an opening extending therethrough that allows the bone-engaging member 114 to extend therethrough and into bone, as discussed in more detail below. As indicated above, a person skilled in the art will appreciate that the base portion can be integrally formed and/or fixedly mated to the bone engaging member.

The side arms of the receiver member can also have various configurations. For example, as shown in FIG. 1B, the side arms 116a, 116b can extend substantially parallel to one another, and an outer surface of each side arm 116a, 116b can be semi-cylindrical. A proximal portion (only portion 116ap is shown) of an outer surface of each of the first and second side arms 116a, 116b can, however, taper inward toward one another. In particular, as best shown in FIG. 1B, an outer surface of a proximal portion of the first and second side arms 116a, 116b ca taper inward, while an inner surface of each side arm 116a, 116b remains equidistant to an inner surface of the other side arm 116a, 116b along the entire length thereof. In an exemplary embodiment, the first and second side arms 116a, 116b taper inward at a location proximal to a distal end 117d of the U-shaped channel 117 and distal to the slots 118a, 118b, which will be discussed in more detail below. The taper can also begin at a location proximal to opposed bores 120a, 120b formed in each side arm 116a, 116b, as will also be discussed in detail below. The angle of the taper can vary. While the angle can vary, in an exemplary embodiment the angle α can be in a range of about 0 to 80 degrees, and more preferably about 0 to 45 degrees, and even more preferably about 0 to 10 degrees. In an exemplary embodiment, the outer surface of each of the first and second side arms tapers inward at an angle α of about 4 degrees, as shown in FIG. 1B.

The side arms 116a, 116b can also have a width extending between the opposed lateral edges that varies along the height of the side arm. In the illustrated embodiment, as best shown in FIG. 1C, each side arm 116a, 116b decreases in width at a proximal portion thereof such that the side arms have a lateral width $x_1$ at the proximal portion (only portion 116ap is shown) that is less than a lateral width $x_2$ of a distal portion (only portion 116ad is shown) of each of the first and second side arms 116a, 116b. As a result, as shown in FIG. 1C, the opposed lateral edges of the proximal portion 116ap of each of the first and second side arms 116a, 116b extends parallel to the opposed lateral edges of the distal portion 116ad of each of the first and second side arms 116a, 116b. Opposed lateral edges of both the proximal portion 116ap and the distal portion 116ad of the first and second side arms 116a, 116b can also be substantially parallel to the longitudinal axis Z of the spinal implant 100.

The dimensions of the receiver member 112 can vary dependent upon the intended use, but in an exemplary embodiment, as shown in FIG. 1B, the receiver member 112 can have a height H measured from a distal-most end of the substantially closed distal portion 112d to a proximal-most end of the open proximal end 112p that is in the range of about 9 mm to 150 mm and more preferably is about 14.5 mm. The substantially closed distal base portion 112d can have a maximum outer diameter D that is in the range of about 8 mm to 16 mm, and more preferably 13 mm. The open proximal end 112p of the receiver member 112 can have a minimum outer diameter $D_p$ that is in the range of about 6 mm to 16 mm, and more preferably about 13 mm. As will be appreciated by a person skilled in the art, the receiver member 112 can be formed from various biocompatible materials including, by way of non-limiting example, surgical grade titanium, surgical grade stainless steel, cobalt chromium, and nitinol.

The receiver member 112 can further include one or more engagement features, such as slots, formed on an external surface of the side arms for mating to various tools. As shown in the embodiment of FIGS. 1A-1D, an outer surface of each of the side arms 116a, 116b of the receiver member 112 includes first and second slots 118a, 118b formed therein for mating to a tool, such as a grasping tool, for example. Though this embodiment shows slots 118a, 118b located in the side arms 116a, 116b, the slots 118a, 118b can alternatively be located in the opposed substantially planar sides 115a, 115b. The slots can have various configurations, but as shown in FIGS. 1A-1C, the slots 118a, 118b extend in a direction transverse to the longitudinal axis Z, and more preferably perpendicular to the longitudinal axis Z. The position of the slots 118a, 118b can vary, but they are preferably positioned proximal to the distal end 117d of the U-shaped channel 117, and in an exemplary embodiment they are thus located on a proximal portion of the outer surface of the side arms 116a, 116b. The position of slots 118a, 118b can depend on the material from which the receiver member is constructed. For example, where the receiver head is formed from a more resilient material, the slots can be positioned closer to the proximal end 112p of the receiver member 112 to allow the receiver member 112 to withstand the forces and pressures placed on the proximal end 112p by an attached tool. The position of slots 118a, 118b is particularly advantageous in that it facilitates engagement of the bone screw assembly 100 by a rod approximator since the grasping tool, for example, does not need to grasp the bone screw assembly 100 underneath the receiver member 112. The position of the slots 118a, 118b also avoids potential contact with adjacent bone structures.

Figure 1F:
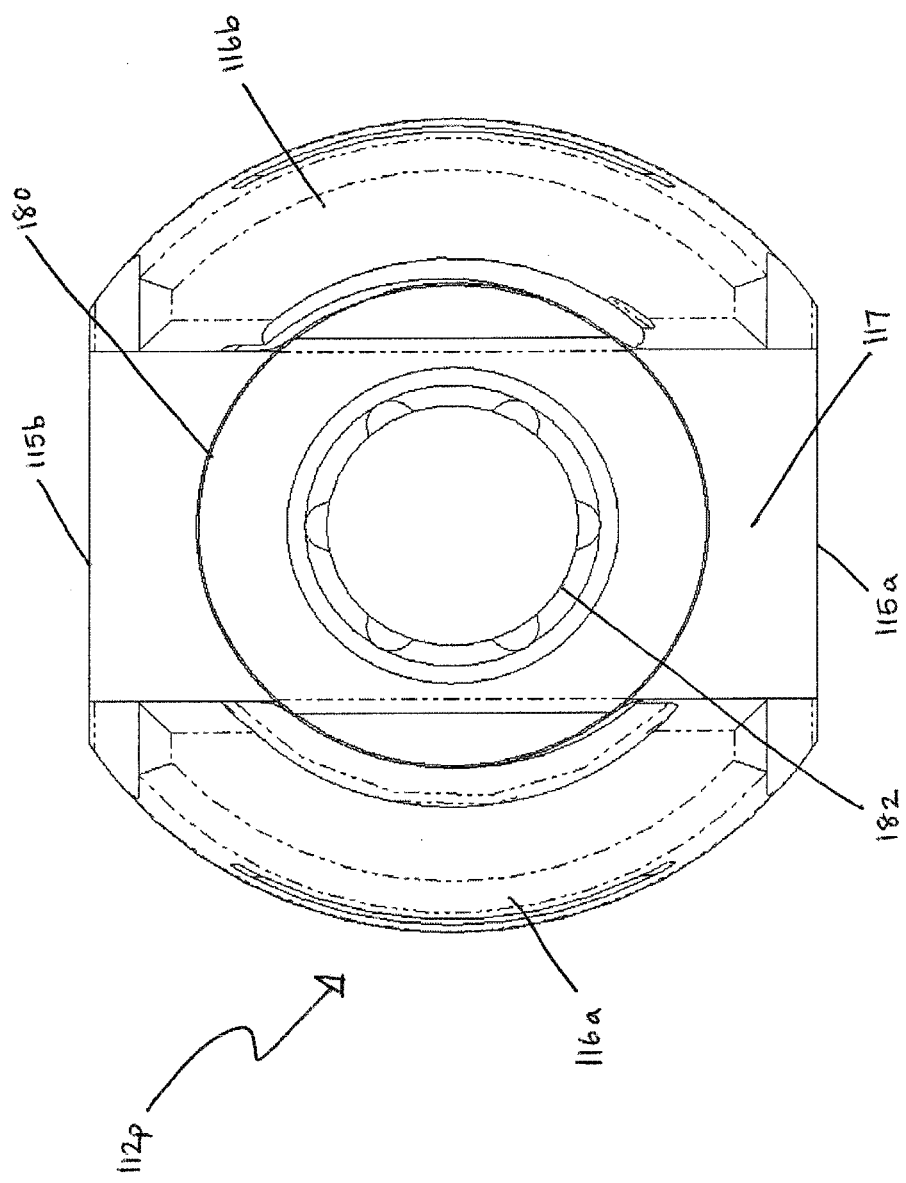
FIG. 1F is a top view of the bone screw assembly of FIG. 1A.
Figure 1G:
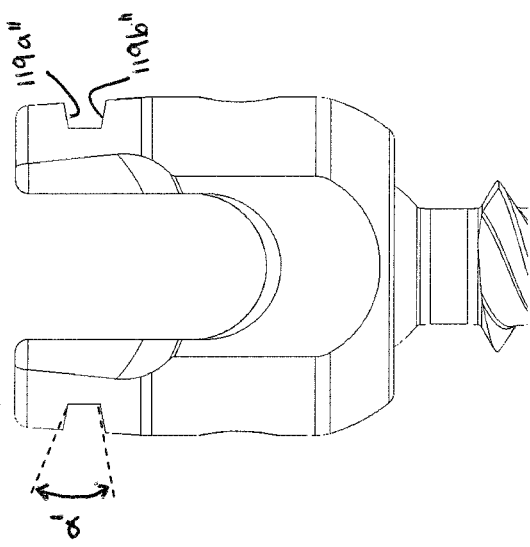
FIG. 1G is a side view of an alternative slot configuration for the bone screw assembly of FIG. 1A.
Figure 1H:
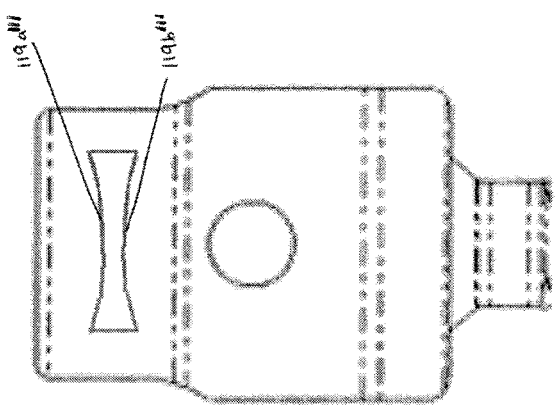
FIG. 1H is a side view of another alternative slot configuration for the bone screw assembly of FIG. 1A.
Figure 1I:
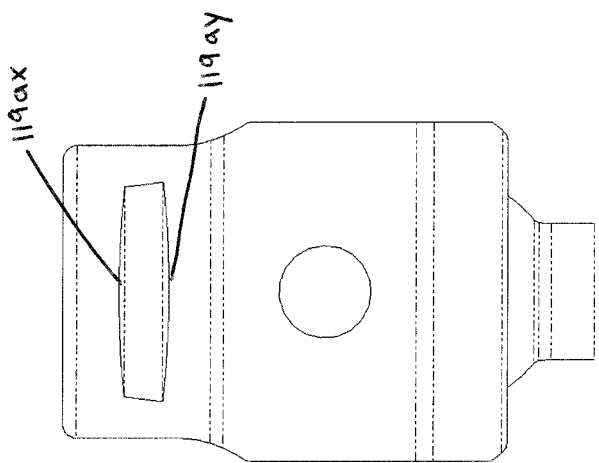
FIG. 1I is a side view of another alternative slot configuration for the bone screw assembly of FIG. 1A.

The slots 118a, 118b can have various shapes and sizes as well, and various cutting techniques can be used to form the slots in the receiver member. In the illustrated embodiment, the slots 118a, 118b are planar cut. In particular, the slots 118a, 118b are made with a cutting tool that forms elongated slots 118a, 118b having opposed upper and lower shoulders or superior and inferior surfaces 119a, 119b, connected by a planar back surface 119c, as shown in FIGS. 1B and 1C. The upper and lower shoulders 119a, 119b can extend parallel to one another along an entire length thereof. The planar back surface 119c can be parallel to the axis Z of the receiver member 112. The upper and lower shoulders 119a, 119 can extend perpendicular to the axis Z of the receiver member 112 and to the planar back surface 119c. In another embodiment, the upper and/or lower shoulders 119a, 119b can extend at an angle greater or less than 90 degrees relative to axis Z. For example, FIG. 1G illustrates an embodiment of opposed slots having upper and lower shoulders 119a", 119b" that are angled relative to one another. While the angle α' can vary, in an exemplary embodiment, the angle α' is in the range of about 0 to 120 degrees, and more preferably about 0 to 50 degrees, and most preferably about 20 degrees. In another embodiment, shown in FIG. 1H, the shoulders 119a''', 119b''' can diverge away from one another at opposed terminal ends of the slots such that each slot has a dovetail shape and a distance between the superior and inferior surfaces is greater at the opposed terminal ends than at the mid-portion of the slot. Alternatively, as shown in FIG. 1I, the shoulders 119ax, 119ay can converge at opposed terminal ends of the slots, such that the midportion has a width between the superior and inferior surfaces that is greater than a width at the ends of the slots. In another embodiment, both the upper and lower shoulders can be substantially planar, but the upper shoulder can include opposed ends that are curved such that they extend proximally away from the lower shoulder. The curved shape of the upper shoulder can allow arms of a tool, such as a grasping member, to be inserted into the slots 118a, 118b at an angle. Though the slots 118a, 118b shown in the embodiment of FIGS. 1A-D are planar cut, they can alternatively be radially cut such that the back surface is curved rather than planar.

The size of each slot 118a, 118b can vary depending on the tool intended to be used with the receiver member. For example, the length of each slot, as measured between opposed terminal ends of the slots 118a, 118b can have a length that is at least about 50% of the width $x_1$ of the arms 116a, 116b. The depth can also vary, but preferably the slots have a depth sufficient to allow a tool to grasp the receiver member 112. In one embodiment, the slots 118a. 118b can have a length in the range of about 2 mm to 12 mm, and a depth in the range of about 0.5 mm to 3 mm.

The bone-engaging member, which anchors the bone screw to bone and can be mated to the receiver member, can also have a variety of configurations. As shown in FIG. 1C, the bone-engaging member 114 is in the form of a bone screw having a proximal head 114p and a distal elongate shank portion 114d with threads 124 formed on an outer surface thereof for engaging bone. The proximal head 114p can have a drive feature on a proximal portion thereof (not shown). In an exemplary embodiment, the drive feature on the proximal head 114p is identical in shape and size to the drive feature of a closure mechanism used to lock the spinal fixation rod in the receiver head, as will be discussed in more detail below. This reduces the number of tools required during surgery. The distal tip of the shank 114d can also have a variety of configurations, and in one embodiment it can be self-tapping. The shank 114d can also be cannulated for advancing the shank over a guidewire, or it can be non-cannulated. The shank 114d can further include one or more fenestrations for allowing a material, such as a cement, to be injected into the shank. The size of the bone-engaging member 114 and the threads 124 can vary depending on the intended use. In certain exemplary embodiments, the bone-engaging member 114 can have a length $L_2$ in the range of about 8 mm to 150 mm. The diameter $D_2$ of the proximal head 114p can vary, and can be in the range of about 4 mm to 10 mm. A minor diameter $d_m$ of the shank 114d can remain constant along the entire length of the shank 114d, or the minor diameter $d_m$ can decrease in a proximal-to-distal direction, as shown in FIGS. 1A and 1B. A major diameter $d_M$ of the shank 114, i.e., the diameter of the threads 124, can also vary, and can remain constant or can likewise taper. The major diameter $d_M$ can be in the range of about 3 mm to 12 mm, and the minor diameter $d_m$ can be in the range of about 2.0 mm to 10 mm. A thread pitch, or number of threads per unit length, can also vary, and in one embodiment the thread pitch can be in the range of about 1 mm to 4 mm. The bone-engaging member 114 can also be formed from various biocompatible materials including, by way of non-limiting example, surgical grade titanium, surgical grade stainless steel, cobalt chromium, and nitinol. It can be formed from either the same or different materials as the receiver member 112. A person skilled in the art will appreciate that, while a bone screw is shown, various other bone implants can be used, such as spinal hooks, cross connectors, plates, staples or fixation element connectors.

The bone-engaging member 114 can be coupled to the receiver in various ways. It can be fixedly mated to and/or integrally formed with the receiver member 112 such that the assembly is monoaxial, or alternatively, the bone-engaging member 114 can be unidirectional or polyaxially coupled to the receiver member 112 to allow angular movement of the receiver member relative to the shank. A variety of techniques can be used to allow angular movement of the receiver member 112 with respect to the bone-engaging member 114. By way of non-limiting example, the proximal head 114p can be hemispherical and can be seated in a concave cavity formed in the base portion of the receiver member 112, with the bone-engaging member 114 extending through the opening formed in the substantially closed distal portion 112d of the receiver member 112 such that in can be angularly oriented relative to the receiver member 112. The proximal head 114p can prevent the bone-engaging member 114 from extending completely through the opening or an additional component may be added to retain the bone engaging member within the receiver. This configuration is illustrated in FIG. 1D. As a result, the bone screw assembly 100 can be assembly using a top loading approach, in which the bone-engaging member 114 is inserted into the top of the receiver member 112 and advanced through the opening in the bottom of the receiver member 112. In an alternative embodiment, the bone screw assembly can be bottom loading, in which the bone-engaging member is inserted into the bottom of the receiver. Such a configuration is illustrated, by way of non-limiting example, in FIG. 1E. As shown, the bone-engaging member 114' has a post 115' at the proximal end, rather than a head. This allows the post 115' to be inserted into the bottom of the receiver 112', and engaged by a separate head 114p'. A person skilled in the art will appreciate that in any embodiment disclosed herein, the bone-engaging member can be top loading or bottom loading.

The implant can also have a compression cap that, when compressed by a spinal fixation element, can lock the bone-engaging member 114 into a fixed position such that it is no longer movable. For example, as shown in FIG. 1C, the bone screw assembly 100 can include a compression cap 130 that is received in the receiver member 112 and configured to be positioned between the proximal head 114p of the bone-engaging member 114, and a spinal fixation element, such as a rod, disposed within the U-shaped channel 117 of the receiver member 112. The compression cap 130 can have a hole formed therethrough such that the drive feature on the proximal head 114p of the bone-engaging member is accessible when the compression cap 130 is disposed within the U-shaped channel 117 over the proximal head 114p. The compression cap 130 can allow free polyaxial movement of the receiver member 112 relative to the shank 114 when a spinal fixation element is disposed within the receiver member 112, and the compression cap 130 can be configured to lock the shank 114 in a fixed orientation relative to the receiver 112 when a closure mechanism 180 is applied to the receiver member 112 to lock the spinal fixation element relative to the receiver 112. In other embodiments, the compression cap can be configured to lock the bone-engaging member in a fixed position relative to the receiver member without locking the spinal fixation element relative to the receiver. A separate closure mechanism can be used to lock the spinal fixation element to the receiver member.

The receiver member 112 can also include features to retain and/or lock the compression cap 130 therein. For example, an outer surface of each side arm 116a, 116b can include first and second bores 120a, 120b formed therein, and an inner sidewall of each arm 116a, 116b can be deformable such that, when a pin or other member is inserted into each bore 120a, 120b, the deformable portion swages inward to engage the compression cap 130 and prevent proximal movement of the compression cap 130 disposed within the receiver member 112. The bores 120a, 120b can be positioned at any location on the receiver member 112. In the illustrated embodiment, the bores 120a, 120b are positioned at a mid-portion of each side arm 116a, 116b, and at a location distal to the first and second slots 118a, 118b. As will be appreciated by a person skilled in the art, the compression cap 130 can be formed from various biocompatible materials including, by way of non-limiting example, surgical grade titanium, surgical grade stainless steel, cobalt chromium, nitinol, PEEK and plastics. It can be formed from either the same or different materials as the receiver member 112 and the bone-engaging member 114.

Various closure mechanisms known in the art can be used to lock a spinal fixation member in the receiver member. The closure mechanism can engage with the receiver member 112 in various ways. For example, as shown in FIG. 1F, the closure mechanism is a set screw 180 that is received in the open proximal end 112p of the receiver member 112, between the side arms 116a, 116b. The receiver member 112 can include various features for mating with a closure mechanism, for example, in an exemplary embodiment, threads 122 on the proximal portion of the inner surface of the side arms 116a, 116b mate with the corresponding threads on the set screw 180 to lock a spinal fixation rod therein, as shown in FIG. 1D. The set screw 180 can also include a drive feature 182 therethrough or located on a proximal portion thereof. As indicated above, the drive feature 182 can match the drive feature of proximal head 114p such that the same tool can be used on both drive features, or the drive feature can be different than that of the proximal head 114p. While a set screw is illustrated, alternative closure mechanisms can be used, e.g., external locking nut, or a combination internal and external, etc. As will be appreciated by a person skilled in the art, the closure mechanism can be formed from various biocompatible materials including, by way of non-limiting example, surgical grade titanium, surgical grade stainless steel, cobalt chromium, and nitinol. It can be formed from either the same or different materials as the receiver member 112, the bone-engaging member 114, and the compression cap 130.

Figure 2D:
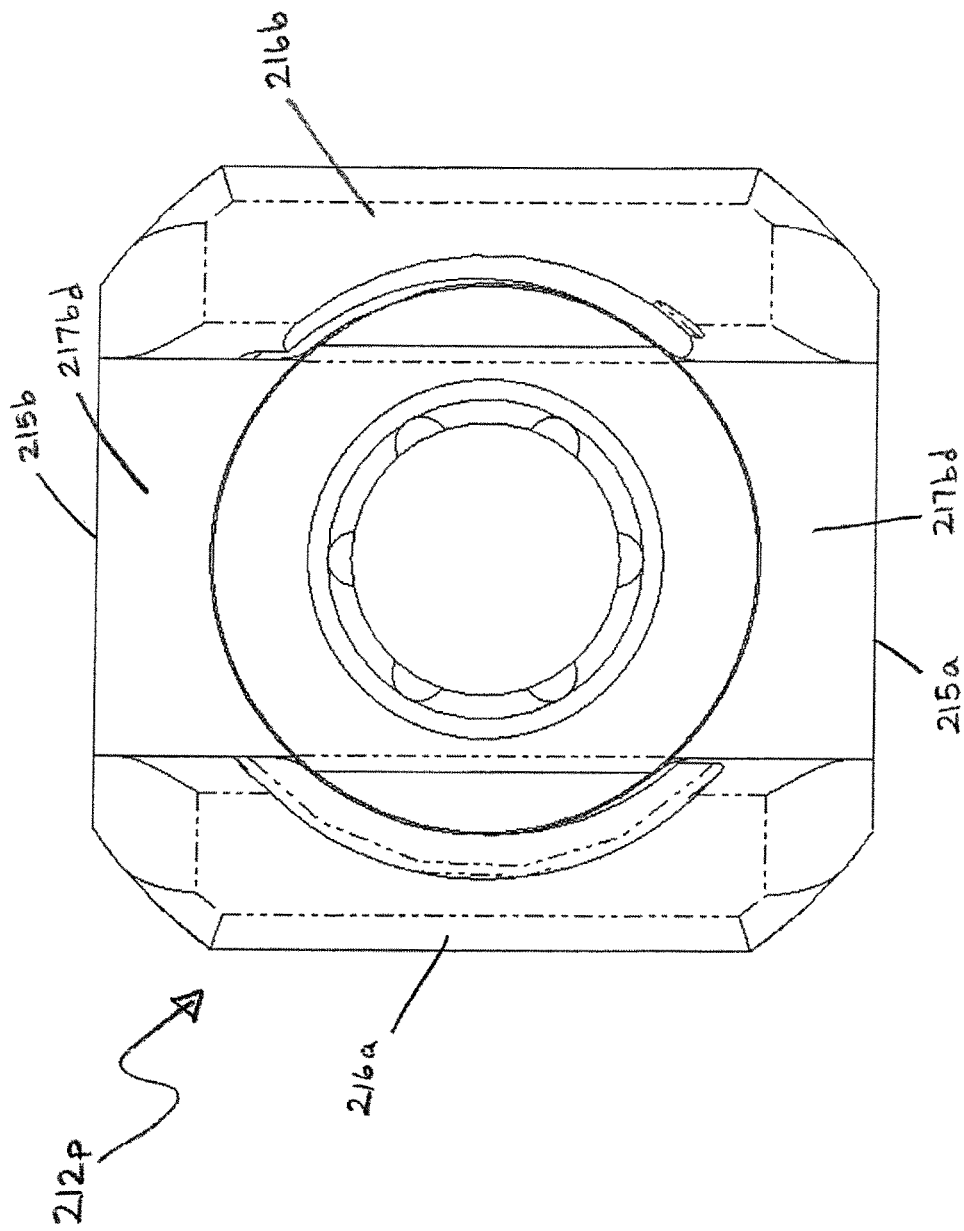
FIG. 2D is a top view of the bone screw assembly of FIG. 2A.

FIGS. 2A-2D illustrate another embodiment of a bone screw assembly 200, which is similar to bone screw assembly 100, having a substantially U-shaped receiver member 212 that has an open proximal end 212p and a substantially closed distal end 212d. Receiver member 212 is similar to receiver member 112 and can thus include any of the features discussed above with respect to receiver 112. For example, receiver member 212 has opposed first and second side arms 216a, 216b that extend proximally from the substantially closed distal end 212d to the open proximal end 212p of the receiver member 212. In this embodiment, however, the first and second side arms 216a, 216b have substantially planar outer surfaces (223a shown in FIG. 2B; 223b shown in FIG. 2D) and substantially cylindrical lateral edges (221a, 221b are shown in FIG. 2B; 221d is shown in FIG. 2C; 221c is not shown). Moreover, in this embodiment receiver member 212 has a generally square shape with first, second, third, and fourth planar sides. In particular, the receiver member 212 has first and second opposed substantially planar sides 215a, 215b extending proximally from the substantially closed distal end 212d and extending between the side arms 216a, 216b, with the side arms 216a, 216b forming third and fourth substantially planar sides. The planar outer surfaces 223a, 223b of the side arms 216a, 216b can be parallel to one another and can each extend parallel to the longitudinal axis Z. The opposed substantially planar sides 215a, 215b extending between the side arms 216a, 216b, and having the U-shaped slots formed therein, can also each extend parallel to the longitudinal axis Z, and they can extend perpendicular to the planar outer surfaces 223a, 223b of side arms 216a, 216b. As indicated above, the bone screw assembly 200 can have a substantially square cross-sectional shape taken in a plane extending perpendicular to the longitudinal axis Z. A proximal portion of the outer surface of each of the first and second side arms 216a, 216b can be substantially the same as a width of a distal portion of the outer surface of each of the first and second side arms 216a, 216b, or in alternative embodiments the arms can taper at any location along the height thereof.

While the particular dimensions of the receiver member can vary, in an exemplary embodiment, the receiver member 212 can have a height $H_2$, measured from a distal end of the substantially closed distal portion 212d to a proximal-most point of the open proximal end 212p, as shown in FIG. 2B, in the range of about 9 mm to 150 mm, and more preferably 14.5 mm. The receiver member 212 can have a maximum diameter $D_2$ in the range of about 8 mm to 16 mm, and more preferably 13 mm.

As with the prior embodiment, the receiver member 212 can also include one or more engagement features for mating to various tools. In this embodiment, the receiver member 212 has first, second, third, and fourth slots separate and distinct slots 218a, 218b, 218c, 218d formed therein. The slots 218a, 218b, 218c, 218d can have various configurations and can be located at various locations on the receiver member 212. For example, the slots 218a, 218b, 218c, 218d can all extend in the same plane and can be spaced equidistance from one another radially around the receiver member 212. In particular, the first side arm 216a can contain the first and second slots 218a, 218b with a gap between them on the planar outer surface 223a, and the second side arm 216b can contain the third and fourth slots 218c, 218d with a gap between them on the planar outer surface 223b. Each slot 218a, 218b, 218c, 218d can be disposed partially across one of the planar outer surfaces 223a, 223b of one of the side arms 216a, 216b and one of the lateral edges 221a, 221b, 221c, 221d on the corresponding side arm 216a, 216b. The four symmetric slots 218a, 218b, 218c, 218d of receiver member 212 can allow certain instruments to engage the receiver member 212 in four distinct orientations, eliminating directionality of instruments. The location can vary, but in the illustrated embodiment the slots 218a, 218b, 218c, 218d can be located proximal to the distal ends 217ad, 217bd of the U-shaped cut-outs 217a, 217b. Preferably, the slots 218a, 218b, 218c, 218d are located as close to the top of the bone screw assembly 200 as possible, but the location can be dependent on factors such as the material from which the receiver member 212 is constructed, as explained above with respect to receiver 112. In an exemplary embodiment, a distance q between the upper shoulder 219a of each slot and the proximal-most end surface 212p of the receiver is in the range of about 1 mm to 10 mm.

The slots 218a, 218b, 218c, 218d can be formed in the receiver member using various techniques. In the embodiment of FIGS. 2A-2D, the slots are radially cut around the receiver member 212, for example, with a cutting tool that has a diameter slightly less than an outer diameter of the receiver member 212. In an exemplary embodiment, the maximum outer diameter of the receiver member is in the range of about 8 mm to 16 mm, and the slots have a diameter that is in the range of about 7 mm to 15 mm. Due to the side arms 216a, 216b having planar surfaces, the slots 218a, 218b, 218c, 218d are only formed along the corners of the square cross-section, i.e., the lateral edges of the side arms 216a, 216b. This results in a gap between slots on a middle portion of each of the planar outer surfaces 223a, 223b. The slots 218a, 218b, 218c, 218d can each have upper and lower shoulders 219a, 219b, which can each be substantially planar, and a curved back surface 219c. The upper and lower shoulders 219a, 219b can be substantially parallel to one another and substantially perpendicular to the longitudinal axis Z. Alternatively, one or both shoulders 219a, 219b can diverge or be curved at a terminal end portion thereof, and/or the shoulders 219a, 219b can extend at an angle relative to one another, e.g., in the range of about 0 degrees to 120 degrees, and more preferably about 0 to 50 degrees, and most preferably about 20 degrees, as previously discussed above with respect to slots 118a, 118b.

Figure 3C:
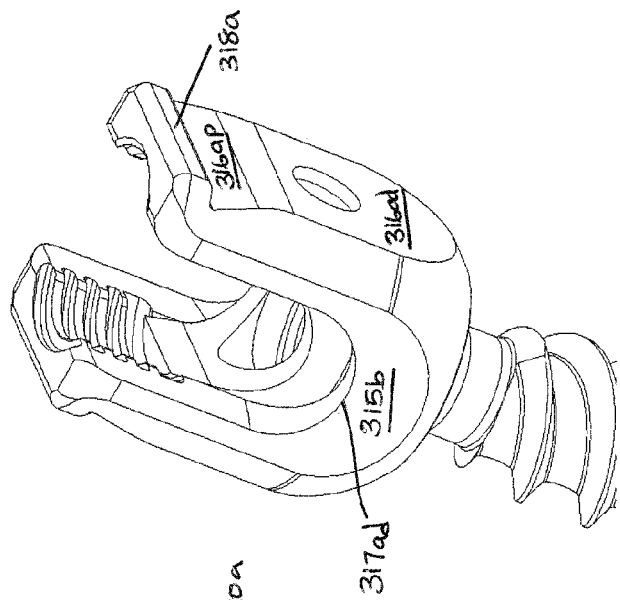
FIG. 3C is an isometric view of the bone screw assembly of FIG. 3A.
Figure 3B:
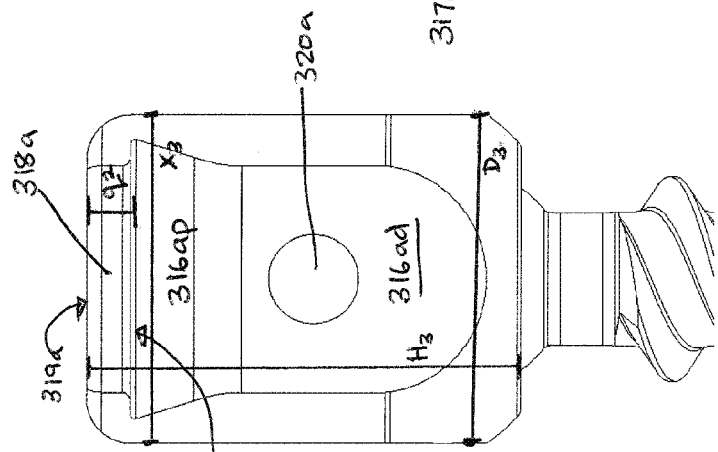
FIG. 3B is a side view of the bone screw assembly of FIG. 3A, rotated 90 degrees.
Figure 3A:
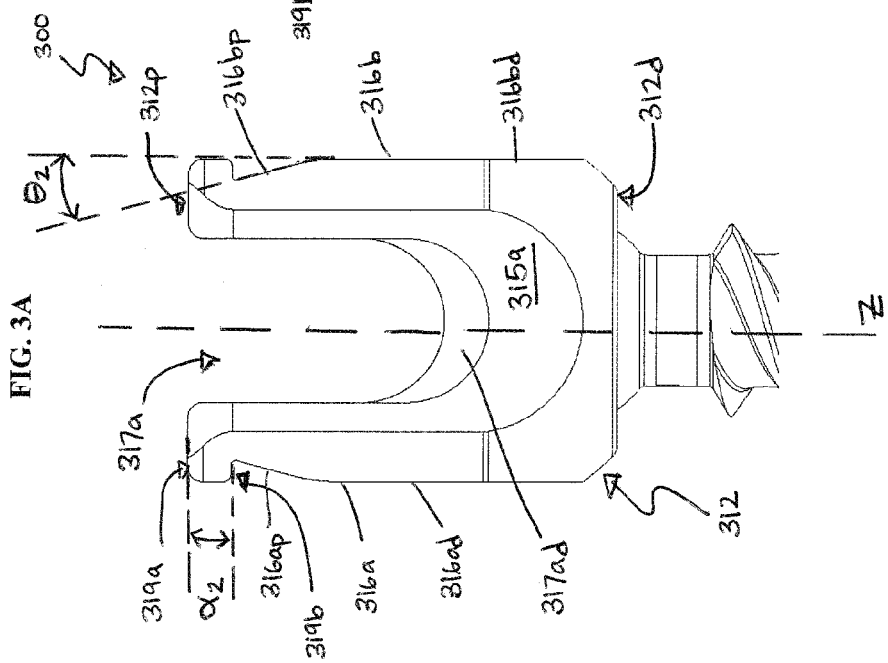
FIG. 3A is a side view of another embodiment of a bone screw assembly having a proximal lip.

FIGS. 3A-3C illustrate another embodiment of a bone screw assembly 300 that is also similar to implant 100 and that has a substantially U-shaped receiver member 312 with an open proximal end 312p and a substantially closed distal end 312d. The bone screw assembly 300 can thus include any of the features previously discussed above with respect to implant 100 and/or bone screw assembly 200. In general, the receiver member 312 has opposed first and second side arms 316a, 316b that extend proximally from the substantially closed distal end 312d to the open proximal end 312p of the receiver member 312. The receiver member 312 can also have opposed substantially planar sides 315a, 315b extending proximally from the substantially closed distal end 312d and between side arms 316a, 316b. A top view of the open proximal end 312p of the side arms 316a, 316b of the receiver member 312 is identical to the top view of the previous embodiment shown in FIG. 2D.

In this embodiment, a portion of each planar outer surface on the first and second opposed side arms 316a, 316b tapers. In particular, each arm 316a, 316b can have a distal planar outer surface 316ad, 316bd and a proximal tapering outer surface 316ap, 316bp that extends proximally from the distal planar outer surface 316ad, 316bd. The distal planar outer surfaces 316ad, 316bd can extend parallel to one another and parallel to a longitudinal axis Z of the bone screw assembly 300, and they can be perpendicular to the open proximal end 312p of receiver member 312. In an exemplary embodiment, inner surfaces of the side arms 316a, 316b remain equidistant to each other along the entire length thereof.

The tapering outer surface 316ap, 316bp can begin at any location, but preferably the taper originates at a location proximal to the bore holes 320a, 320b formed in the side arms 316a, 316b. The tapering outer surfaces 316a, 316p can taper inward proximally at various angles. In an exemplary embodiment, each tapering outer surface 316ap, 316bp tapers inward at an angle $\theta_2$ as measured from a plane of the distal planar outer surface 316ad, 316bd. While the angle can vary, in an exemplary embodiment the taper angle $\theta_2$ is in the range of about 0 to 80 degrees, and more preferably about 0 to 45 degrees, and even more preferably about 10 degrees. In an exemplary embodiment, the angle $\theta_2$ is about 4 degrees.

The tapering outer surface 316ap, 316bp of each side arm 316a, 316b can terminate at a location just distal to the proximal-most end of the receiver member, such that each side arms 316a, 316b includes a proximal lip 318a, 318b formed thereon extending between opposed lateral edges of the side arm 316a, 316b at proximal end 312p. Each lip can have a width that is substantially the same as a width of the side arms 316a, 316b. The proximal lip 318a, 318b can have an inferior surface 319b that abuts the tapering outer surface 316ap, 316bp. The proximal lip can also have a superior surface 319a that is located at the proximal end 312p of the receiver member 312. As shown in the embodiment of FIGS. 3A-3C, the inferior surface 319b can be located a distance $q_2$ from the superior surface 319a, and thus from the proximal end 312p. In an exemplary embodiment, the distance $q_2$ between the inferior surface 319b of the proximal lip 318a, 318b is in the range of about 1 mm to 4 mm, making the proximal lip 318a, 318b of this embodiment relatively narrow. One reason this is possible is that that the proximal lip 318a, 318b can provide a more robust attachment than other grasping elements, such as slots, on the receiver member 312 for instruments to grasp due to the length of the proximal lip 318a, 318b. In particular, the proximal lip 318a, 318b can provide more material, i.e., an entire width of a side arm 316a, 316b for attachment and can thereby accommodate a thinner profile than, for example, the slots 218a, 218b, 218c, 218d in the previous embodiment, which each only provide a corner of the receiver member 212 for an instrument to grasp. The greater surface area for grasping provided by the proximal lip 318a, 318b allows for a narrower distance $q_2$ between the grasping element and the proximal end 312p than in other embodiments which have smaller surface areas for grasping, e.g., the distance q in receiver member 212. The superior and inferior surfaces 319a, 319b of the proximal lip 318, 318b can be parallel to each other and can be perpendicular to the longitudinal axis Z of the receiver member. Alternatively, the inferior surface 319b can extend at an angle $\alpha_2$ relative to a superior surface 319a of the proximal lip. While the angle $\alpha_2$ can vary, in one embodiment the angle $\alpha_2$ can be in the range of about 0 to 89 degrees, and more preferably about 0 to 30 degrees, and most preferably the angle is about 10 degrees. A person skilled in the art will appreciate that the angle $\alpha_2$ can result from one or both surfaces 319a, 319b extending at an angle other than 90 degrees relative to the axis z.

In this embodiment, the receiver member 312 can have a height $H_3$, measured from a distal end of the substantially closed distal portion 312d to a proximal-most point of the open proximal end 312p, as shown in FIG. 3B, in the range of about 9 mm to 150 mm but is preferably about 14.5 mm. The substantially closed distal base portion 312d can have a diameter $D_3$ ranging from about 8 mm to 16 mm, but is preferably around 13 mm. A width $x_3$ of the tapering outer surface 316ap, 316bp of each of the first and second side arms 316a, 316b can be substantially the same as the width $D_3$ of the distal planar outer surfaces 316ad, 316bd.

The illustrated spinal implants can be used to stabilize a variety of bone structures, including by way of non limiting example, vertebral bodies, lateral masses, lamina and transverse process. Where the desired use of the spinal implant is for implantation in a bony element, the first step is positioning and driving the anchor, e.g., the bone screw, to the desired depth in the vertebra. When the bone screw is cannulated, a guidewire can be used to position the bone screw. The cannulated bone screw can be advanced over the guidewire, which allows placement of the bone screw at a desired depth in bone. A pre-drilled hole can optionally be formed prior to advancing the bone screw over the guidewire. In addition to the cannulation, the bone screw could have one or more fenestrations formed therein for allowing a material, such as a cement, to be injected into the bone screw to enhance fixation. When the bone screw is non-cannulated, the screw is preferably inserted into a hole that is pre-drilled in bone using a drilling tool. Both cannulated and non-cannulated screws can be self-tapping to allow the screw to drive through bone. A person skilled in the art will appreciate that various techniques known in the art can be used to implant the bone screw in bone.

In use, when two bone screws are fixed in adjacent vertebra, a spinal fixation element can be inserted into the receiver member of each screw. It can be difficult to position the spinal fixation element within each receiver member because of the alignment of the bone screws and the dimensions of the surgical site. As a result, a rod approximator or reduction device can be used to place the fixation element in the receiver members. For example, the arms of the rod approximator device can include a grasping member with arms that contain grasping elements that fit into the corresponding recesses on the receiver member of the bone screw, stabilizing the rod approximator relative to the bone screw. With the rod pusher member in a first, proximal position, the device can be manipulated to place the spinal rod between a rod engaging member and the receiver member. The rod approximator can also include first and second handle members that can be grasped and squeezed together to cause the rod pusher member to move to a second, distal position, thereby causing the rod engaging member to grasp and push the fixation rod into the receiver member of the bone screw. After the rod is advanced into the receiver member, a closure mechanism can be applied to the receiver member of the bone screw to secure the rod.

Figure 4:
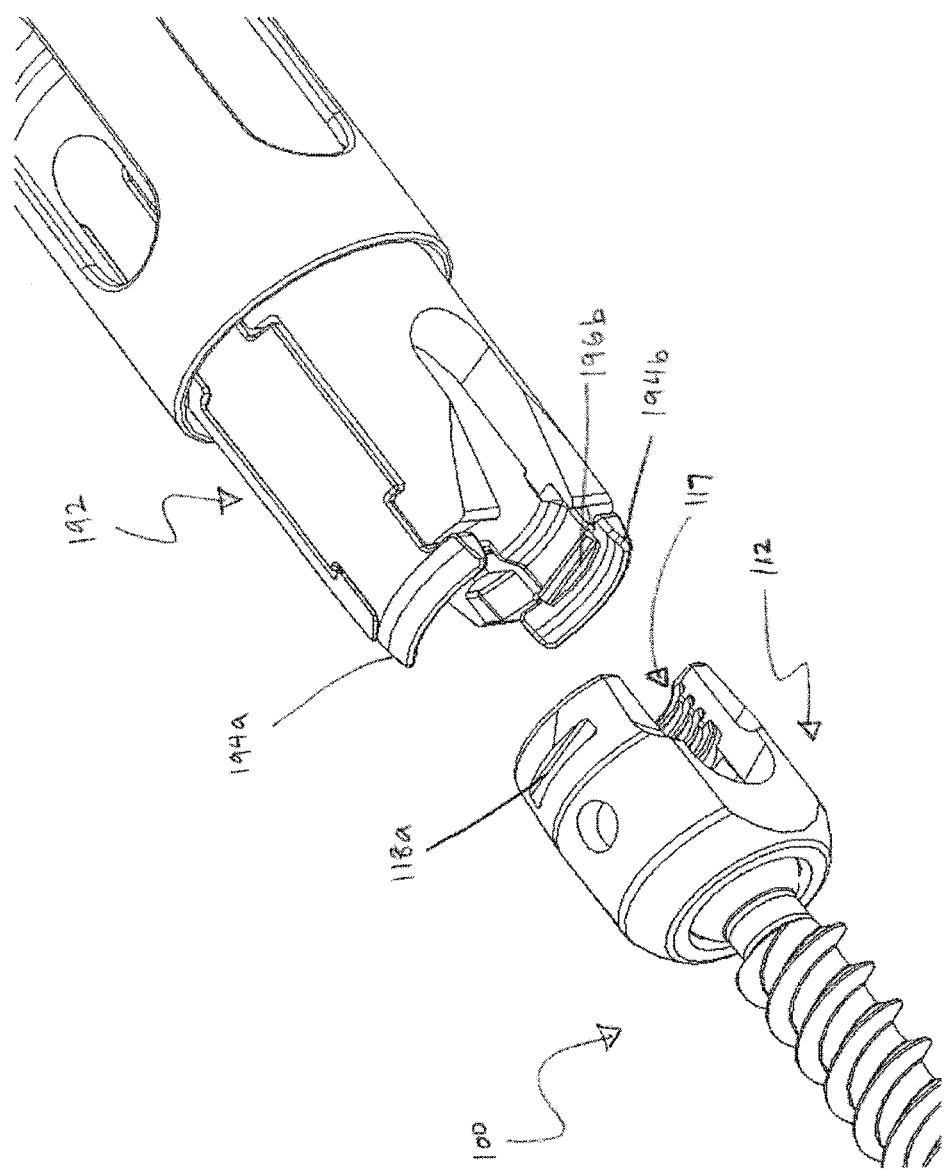
FIG. 4 is a perspective view of a tool for mating with the bone screw assembly of FIG. 1A.
Figure 5:
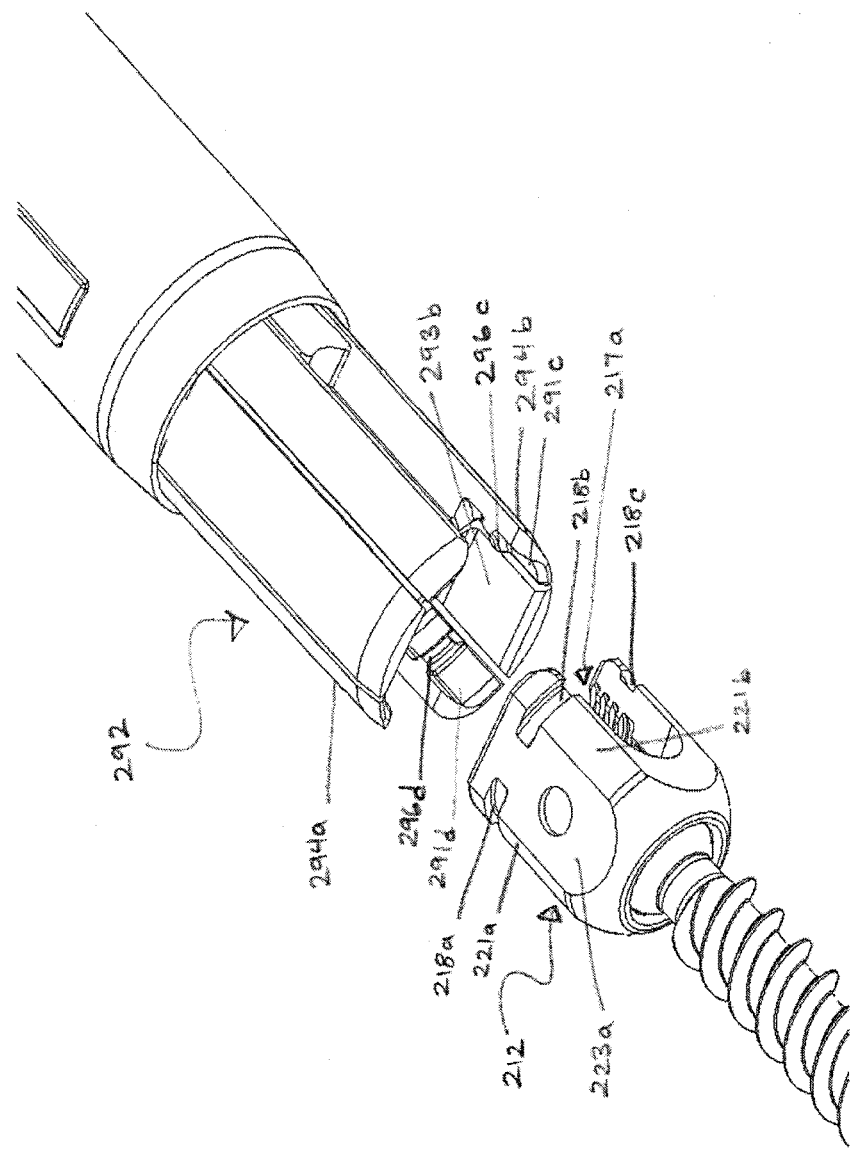
FIG. 5 is a perspective view of a tool for mating with the bone screw assembly of FIG. 2A.
Figure 6:
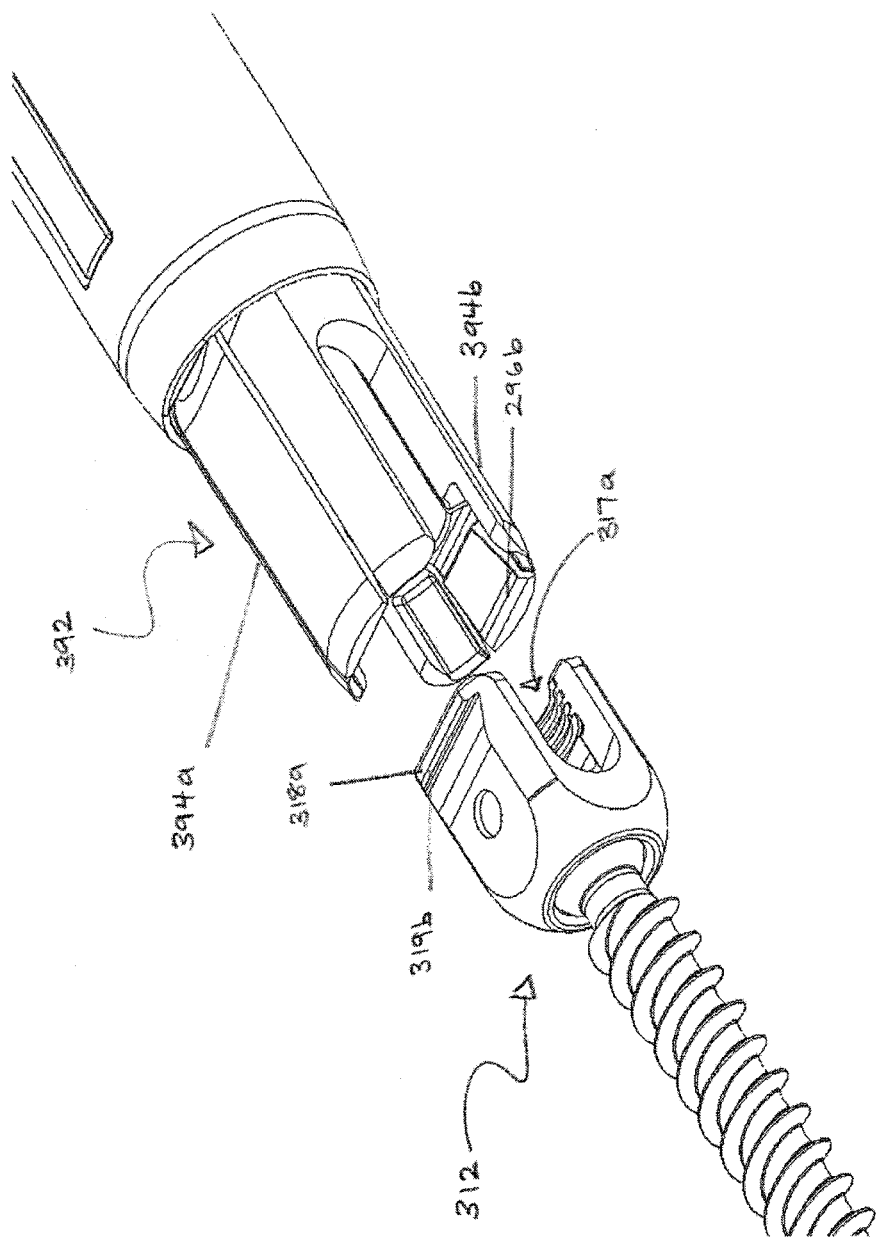
FIG. 6 is a perspective view of a tool for mating with the bone screw assembly of FIG. 3A.

FIGS. 4-6 illustrates a distal portion of a tool for grasping the receiver member of a spinal anchor, such as the bone screw assemblies shown in FIGS. 1A, 2A, and 3A. A person skilled in the art will appreciate that the tools shown in FIGS. 4-6 are intended to represent any type of tool used to grasp an implant. Such tools can generally include features as shown that are configured to fit into and engage corresponding mating features shown in the spinal implants.

For example, FIG. 4 illustrates a rod approximator device 190 that can be used to grasp and stabilize receiver member 112, while pushing the spinal fixation element into the U-shaped channel 117 formed in the receiver member 112 of the spinal implant 100. The device 190 can also be used to hold the bone screw assembly 100, while the closure mechanism 180 is threaded into the receiver member 112 of the spinal implant 100 to secure the stabilizing rod in the U-shaped channel 117, and thereby lock the receiver member 112 in a fixed position relative to the bone screw. As shown, the rod approximator device 190 has opposed arms 194a, 194b located on a distal end of a grasping member 192 that are configured to surround and grasp the proximal portion 116ap, 116bp of the receiver member 112. The arms 194a, 194b can have grasping elements 196a, 196b formed on an inner surface thereof, such that grasping elements 196a, 196b can mate with corresponding slots 118a, 118b of the receiver member 112 of the implant 100. In this embodiment, the grasping elements 196a, 196b are in the form of protrusions that have en elongate length with a shape and size configured to match the shape and size of the cavity defined by the slots 118a, 118b. The inner surface of arms 194a, 194b can taper inward in a distal-to-proximal direction such that it corresponds with the taper of the proximal portion 116ap, 116bp of side arms 116.

FIG. 5 illustrates another embodiment of a rod approximator device 290 for use with bone screw assembly 200. As shown, the device 290 has opposed arms 294a, 294b, located on a distal end of a grasping member 292, that are configured to surround and grasp the proximal portion of the side arms 216a, 216b of the receiver member 212. The arms 294a, 294b can have grasping elements 296a, 296b, 296c, 296d formed on an inner surface thereof, such that grasping elements 296a, 296b, 296c, 296d can mate with corresponding slots 218a, 218b, 218c, 218d of the receiver member 212 of the bone screw assembly 200. In this embodiment, the grasping elements 296a, 296b, 296c, 296d are in the form of four separate and distinct protrusions that are positioned, shaped, and sized to correspond to the slots 218a, 218b, 218c, 218d of the receiver member 212. The inner surface of arms 194a, 194b can mirror the planar and semi-cylindrical outer surfaces of the receiver member 212. The four symmetric slots 218a, 218b, 218c, 218d of receiver member 212 can allow certain instruments, such as the grasping member 292, to engage the receiver member 212 in four distinct orientations, eliminating directionality and allowing a user to choose the direction of the connection. Some instruments can only engage the receiver member 212 in four distinct orientations when there is no rod located in the U-shaped cut-outs 217a, 217b, and some instruments have rod slots, in which it would be desirable to engage the receiver member 212 in only two of the four distinct orientations to align the rod slots with the U-shaped cut-outs 217a, 217b. A spinal fixation rod can be pushed into the U-shaped cut-outs 217a, 217b formed in the receiver member 212 of the bone screw assembly 200, and a closure mechanism 180 can be threaded into the receiver member 212 of the bone screw assembly 200, while device 290 is stabilizing the bone screw assembly 200 with respect to the spinal fixation element.

FIG. 6 illustrates one embodiment of a rod approximator device 390 for use with bone screw assembly 300. In this embodiment, the arms 394a, 394b located on the distal end of a grasping member 392 can surround and grasp the tapering outer surface 316ap, 316bp of the receiver member 312. As shown, the arms 394a, 394b have grasping elements 396a, 396b formed on an inner surface thereof, such that grasping elements 396a, 396b can mate with the corresponding slots under the inferior surface 319b of the proximal lip 318a, 318b of the receiver member 312 of the bone screw assembly 300. The grasping elements 396a, 396b can be in the form of elongate rectangular protrusions that are positioned, shaped, and sized to correspond to the slots. The inner surface of arms 394a, 394b can taper inward in a distal-to-proximal direction such that it corresponds with the taper of the tapering outer surface 316ap, 316bp of the side arms 316a, 316b. The bone screw assembly 300 can be stabilized while the spinal fixation element is pushed into the U-shaped rod-receiving recesses 317a, 317b formed in the receiver member 312 of the bone screw assembly 300 and while the closure mechanism 180 can be threaded into the receiver member 312 of the bone screw assembly 300 to secure the stabilizing rod in the U-shaped rod-receiving recesses 317a, 317b.

Although the bone anchors can be used in a pedicle, a person skilled in the art will appreciate that the bone anchors disclosed herein can be used in all types of human skeletal structures. This includes, by way of non-limiting examples, vertebra, femur, tibia, hip, and skull.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A bone anchor, comprising:
a bone-engaging member effective to engage bone;
a receiver member from which the bone-engaging member extends distally, the receiver member having first and second opposed side arms separated by opposed U-shaped slots that define a U-shaped channel for receiving a spinal fixation element; and
first and second recesses formed in outer surfaces of the first and second opposed side arms of the receiver member, the first and second recesses extending laterally across the outer surfaces of the first and second arms, respectively, and transverse to a central longitudinal axis of the receiver member, such that latitudinal dimensions of the recesses are greater than longitudinal dimensions of the recesses;
wherein the outer surfaces of the first and second side arms each include a continuously tapered portion that tapers inward towards the central longitudinal axis of the receiver member;
wherein the first and second recesses are formed in the continuously tapered portions of the outer surfaces of the first and second opposed side arms; and
wherein the receiver member includes first and second opposed planar outer surfaces that are each disposed distal to the U-shaped slots, between opposed lateral edges of the first and second side arms, and distal to the first and second recesses.

2. The bone anchor of claim 1, wherein the tapered portions are proximal to a distal-most end of the U-shaped recesses.

3. The bone anchor of claim 1, wherein the tapered portions are closer to one another at a proximal end thereof.

4. The bone anchor of claim 1, wherein the tapered portions are formed in a proximal-most portion of the receiver member.

5. The bone anchor of claim 1, wherein at least a portion of the outer surfaces of the first and second opposed side arms defines a portion of a cylinder.

6. The bone anchor of claim 1, wherein the tapered portions taper inward at an angle of about 4 degrees.

7. The bone anchor of claim 1, further comprising first and second bores formed in the outer surfaces of the first and second side arms, the bores being located distal to the first and second recesses.

8. The bone anchor of claim 1, wherein the bone-engaging member is one of:
formed integrally with the receiver member;
limited to uniplanar movement with respect to the receiver member; and
polyaxially movable with respect to the receiver member.

9. The bone anchor of claim 1, wherein each of the continuously tapered portions includes a tapered portion that is proximal to the recesses and a tapered portion that is distal to the recesses, the proximal and distal portions tapering at the same angle.

10. A bone anchor, comprising:
a bone-engaging member effective to engage bone;
a receiver member from which the bone-engaging member extends distally, the receiver member being configured to receive a spinal fixation element and having first and second opposed side arms; and
first and second recesses formed in outer surfaces of the first and second opposed side arms of the receiver member;
wherein the outer surfaces of the first and second side arms each include a continuously tapered portion that tapers inward towards a central longitudinal axis of the receiver member;
wherein the first and second recesses are formed in the continuously tapered portions of the outer surfaces of the first and second opposed side arms, and
wherein the first recess has a planar back surface that is parallel to the central longitudinal axis of the receiver member and to a planar back surface of the second recess.

11. A bone anchor, comprising:
a threaded distal shaft portion; and
a proximal receiver member from which the distal shaft portion extends, the receiver member having first and second arms that define a rod-receiving recess therebetween;
wherein the first arm includes a first outer surface with a first tapered proximal portion having a first slot formed therein, the first slot extending laterally across the outer surface of the first arm and transverse to a central longitudinal axis of the receiver member such that a latitudinal dimension of the first slot is greater than a longitudinal dimension of the first slot;

wherein the second arm includes a second outer surface with a second tapered proximal portion having a second slot formed therein, the second slot extending laterally across the outer surface of the second arm and transverse to the central longitudinal axis of the receiver member such that a latitudinal dimension of the second slot is greater than a longitudinal dimension of the second slot;

wherein the tapered proximal portions of the first and second arms taper continuously and towards one another in a proximal direction; and wherein the receiver member includes two opposed planar side walls that each extends between opposed lateral edges of the first and second arms, distal to the rod-receiving recess, and distal to the first and second slots.

12. The bone anchor of claim 11, wherein each of the first and second slots has opposed upper and lower surfaces, and wherein the upper and lower surfaces are parallel to one another along an entire length thereof.

13. The bone anchor of claim 11, wherein each of the first and second slots has opposed upper and lower surfaces, and wherein the upper and lower surfaces diverge away from one another at opposed ends thereof.

14. The bone anchor of claim 11, wherein each of the first and second slots has opposed upper and lower surfaces, and wherein the upper and lower surfaces extend at an angle with respect to one another in the range of about 0 to about 50 degrees.

15. The bone anchor of claim 11, wherein a distance between a proximal end of the tapered portion of the first arm and a proximal end of the tapered portion of the second arm is less than a distance between a distal end of the tapered portion of the first arm and a distal end of the tapered portion of the second arm.

16. The bone anchor of claim 11, wherein at least a portion of the outer surfaces of the first and second opposed side arms defines a portion of a cylinder.

17. The bone anchor of claim 11,
wherein the first continuously tapered portion includes a tapered portion that is proximal to the first slot and a tapered portion that is distal to the first slot, the proximal and distal portions tapering at the same angle, and wherein the second continuously tapered portion includes a tapered portion that is proximal to the second slot and a tapered portion that is distal to the second slot, the proximal and distal portions tapering at the same angle.

18. The bone anchor of claim 11, further comprising first and second bores formed in the outer surfaces of the first and second arms of the receiver member, the first and second bores being positioned distal to the first and second slots.

19. A bone anchor, comprising:
a threaded distal shaft portion; and
a proximal receiver member from which the distal shaft portion extends, the receiver member having first and second arms that define a rod-receiving recess therebetween;

wherein the first arm includes a first outer surface with a first tapered proximal portion having a first slot formed therein;

wherein the second arm includes a second outer surface with a second tapered proximal portion having a second slot formed therein;

wherein the tapered proximal portions of the first and second arms taper continuously and towards one another in a proximal direction, wherein the first and second slots extend transverse to a central longitudinal axis of the receiver member, and wherein the first slot has a planar back surface that is parallel to the central longitudinal axis of the receiver member and to a planar back surface of the second slot.

* * * * *